(12) United States Patent
Andersen

(10) Patent No.: US 10,765,337 B2
(45) Date of Patent: Sep. 8, 2020

(54) EAR CANAL PLUG FOR DETECTING BIO-ELECTRICAL SIGNALS

(71) Applicant: T&W Engineering A/S, Lynge (DK)

(72) Inventor: Mikael Andersen, Allerod (DK)

(73) Assignee: T&W Engineering A/S, Lynge (DK)

( * ) Notice: Subject to any disclaimer, the term of this patent is extended or adjusted under 35 U.S.C. 154(b) by 0 days.

(21) Appl. No.: 15/938,499

(22) Filed: Mar. 28, 2018

(65) Prior Publication Data

US 2018/0206788 A1 Jul. 26, 2018

Related U.S. Application Data

(63) Continuation-in-part of application No. PCT/EP2015/072691, filed on Oct. 1, 2015.

(51) Int. Cl.
*A61B 5/00* (2006.01)
*A61B 5/0478* (2006.01)
*H04R 25/00* (2006.01)

(52) U.S. Cl.
CPC .......... *A61B 5/0478* (2013.01); *A61B 5/6817* (2013.01); *A61B 5/6847* (2013.01); *A61B 5/6867* (2013.01); *H04R 25/652* (2013.01); *H04R 25/658* (2013.01); *A61B 2562/125* (2013.01); *H04R 25/65* (2013.01)

(58) Field of Classification Search
CPC ... A61B 5/0478; A61B 5/6847; A61B 5/6867; A61B 5/6817
USPC ...................................................... 600/379
See application file for complete search history.

(56) References Cited

U.S. PATENT DOCUMENTS

| 6,475,214 B1 | 11/2002 | Moaddeb |
| 2010/0324355 A1* | 12/2010 | Spitaels ............... H04R 25/606 600/25 |
| 2012/0209101 A1 | 8/2012 | Kidmose et al. |
| 2013/0035578 A1 | 2/2013 | Chiu et al. |
| 2014/0171775 A1 | 6/2014 | Kilsgaard et al. |

FOREIGN PATENT DOCUMENTS

| JP | 2001299713 A | 10/2001 |
| JP | 2002119519 A | 4/2002 |
| JP | 2010504159 A | 2/2010 |

(Continued)

OTHER PUBLICATIONS

N.S. Dias et al., "New dry electrodes based on iridium oxide (IrO) for non-invasive biopotential recordings and stimulation", Sensors and Actuators A:Physical, Nov. 1, 2010, pp. 28-34, vol. 164; No. 1-2.

(Continued)

*Primary Examiner* — Lee S Cohen
(74) *Attorney, Agent, or Firm* — Sughrue Mion, PLLC

(57) ABSTRACT

An ear plug for arrangement in an ear canal includes at least two electrodes for detecting an EEG signal from a skin surface when the ear plug is arranged in the ear canal. The ear plug further includes a housing having an outer wall made from a resilient material, and a signal acquisition circuit. The electrodes are provided with a skin contact part arranged on an outside surface of the housing and connected through the outer wall of the housing to a supporting member on the inner part of the housing. The skin contact part and the supporting member are arranged for clamping the outer wall.

19 Claims, 8 Drawing Sheets

(56) References Cited

FOREIGN PATENT DOCUMENTS

| | | | |
|---|---|---|---|
| JP | 2012120705 A | 6/2012 |
| JP | 2012530563 A | 12/2012 |
| JP | 2012533248 A | 12/2012 |
| JP | 2014008166 A | 1/2014 |
| WO | 2007/047667 A2 | 4/2007 |
| WO | 2008/036460 A1 | 3/2008 |
| WO | 2011/000383 A1 | 1/2011 |
| WO | 2011/006681 A1 | 1/2011 |
| WO | 2013/026481 A1 | 2/2013 |
| WO | 2015/036288 A1 | 3/2015 |

OTHER PUBLICATIONS

International Search Report for PCT/EP2015/072691 dated Jun. 21, 2016 [PCT/ISA/210].
Written Opinion for PCT/EP2015/072691 dated Jun. 21, 2016 [PCT/ISA/237].
Communication dated Mar. 26, 2019, from the Japanese Patent Office in counterpart application No. 2018-514426.
Communication dated Dec. 5, 2019 in Singapore Application No. 11201801721V.

* cited by examiner

EAR CANAL PLUG FOR DETECTING BIO-ELECTRICAL SIGNALS

This application is a continuation-in-part of Application No. PCT/EP2015/072691 filed Oct. 1, 2015, the disclosure of which is incorporated by reference herein.

BACKGROUND OF THE INVENTION

The present invention relates to an ear plug for detecting bio-electrical signals. The invention relates more particularly to an ear plug for arrangement in an ear canal, where the ear plug comprises at least two electrodes prepared for detecting an EEG signal from a skin surface when the ear plug is arranged in the ear canal. The ear plug also comprises a housing with an outer wall made from a resilient material, and further comprises a signal acquisition circuit. The invention also relates to a method for manufacturing the ear plug.

Bio-electrical signals are here understood to be electrical potential differences across a tissue, organ or cell system or originating from the human body. The best known examples are Electrocardiogram (ECG) signals and Electroencephalogram (EEG) signals. An ear plug for detecting bio-electrical signals in the ear canal is made for arrangement fully or partly in the ear canal of a person. The ear plug is mainly designed for the detection of EEG signals.

EEG signals are electrical signals generated by a person's brain activity. In recent years, EEG monitoring systems, that may be carried or worn continuously by a person to be monitored, have been devised. A goal is to have personal wearable EEG monitors which can be carried without causing more inconvenience than glasses or a modern small hearing aid, even when carried over an extended interval of time, e.g. several months or years.

Such EEG monitors may be applied for purposes of surveillance of a condition of the person and for providing some kind of alarm or information in case predetermined conditions are met. The monitor may also be applied for collection of data for further analysis, e.g. for diagnostic purposes or for research use. An example of an application is for surveillance of persons having diabetes.

Measuring the EEG signal in the ear canal is known from WO 2011/000383 A1 disclosing an ear plug with EEG electrodes where the ear plug shape is individually matched to the users ear canal.

In WO 2013/026481 A1 it is described that the electrodes can be capacitive, i.e. being provided with a dielectric material on the surface intended to contact the skin surface.

WO 2007/047667 A2 discloses an ear plug made from a compressible material and provided with EEG electrodes.

One problem with the known solutions is that it is difficult to obtain an ear plug with EEG electrodes which is both pleasant and not annoying to wear for extended periods of time, and at the same time can obtain a stable and reliable EEG signal.

SUMMARY OF THE INVENTION

A solution to this problem has been found by an ear plug further having electrodes provided with a skin contact part arranged on an outside surface of the ear plug housing and connected through the outer wall of the housing to a supporting member on the inner part of the housing. The skin contact part and the supporting member are arranged for clamping the outer wall.

One advantage of the solution is that a flexible ear plug which will adapt the shape of the ear canal is achieved.

When the outer wall of the ear plug housing is said to be made from a resilient material, this is understood to include elastic as well as viscoelastic materials In an embodiment of the ear plug the housing is compressible and the electrodes are arranged to follow a movement caused by a compression of the outer wall. This has the advantage that the whole ear plug is compressible as such, and not just the resilient outer wall. Thereby, the risk that the ear plug becomes irritating or annoying to wear over an extended period of time, such as several month or years, becomes significantly reduced.

In a further embodiment of the ear plug the outer wall of the housing is provided with a shape customized to the ear canal of an intended user. This will also make the ear plug more pleasant to wear and reduce the risk of annoyance or irritation.

In a further embodiment of the ear plug the skin contact part of the electrodes is provided with a layer of iridium oxide on at least the surface intended to touch the skin surface in ear, e.g. the ear canal or concha part of the ear. This has the advantage that a low impedance between skin and electrode can be achieved, and that the risk of skin irritation is reduced. One advantage of iridium oxide is that a relatively small geometric area of an electrode can be applied, and still achieving a large electrochemically effective area. When the layer of iridium oxide also comprises tantalum, these advantages are more profound. Concerning the low impedance, this is also the case when the layer of iridium oxide is porous.

In a further embodiment of the ear plug each one of the at least two electrodes are provided with an amplifying circuit, the amplifying circuit being shielded against electromagnetic noise. Thereby the electrodes are made into so called active electrodes, where the signal delivered from the electrode is more powerful and therefore less sensitive to noise. The amplifying circuit may also have an analogue to digital (A/D) converter, making the signal from the electrode even less sensitive to noise.

In a further embodiment of the ear plug the amplifying circuit of the electrodes is connected to a flex print circuit combining the signals from the at least two electrodes. This provides for a mechanically flexible electronic platform, which can follow compressions of the ear plug including the electrodes. This flexible electronic platform can also be applied for mounting in individually fitted ear plugs. Flexibility of the electronic platform can also be achieved by use of wires, but this will be more time consuming in the production process.

In a further embodiment of the ear plug the skin contact part of the electrodes is detachabliy connected to the supporting member of the electrodes through a connecting part. This allows for assembling of the electrodes through holes in the outer wall of the ear plug housing.

In a further embodiment of the ear plug, the outer wall is adapted to exert a pressure against the ear canal wall when inserted, in order to facilitate good electrical contact between the skin contact parts of the electrodes and the ear canal wall.

In general the use of a conductive gel may be applied for improving the electrical connection between an EEG electrode and the skin of the ear canal.

In an embodiment an ear plug as described above is applied for an EEG monitor. The ear plug may comprise the whole EEG monitor, or the ear plug may comprise some electrodes, while signal processing, power supply, speaker for notifications etc. could be arranged in a separate housing, e.g. to be arranged behind the ear.

In another embodiment an ear plug described above is applied for a hearing aid in which an EEG signal is detected and utilized by the hearing aid. The utilization may be for better adjustment of the hearing aid or for automatic program selection. This can be an in the ear hearing aid, or for another hearing aid comprising an ear plug part.

In a second aspect the invention is directed at a method for manufacturing an ear plug. This method comprises the steps: 1) providing an ear plug housing with a resilient outer wall; 2) providing EEG electrodes, where each electrode is separated into a skin contact part and a supporting member; 3) connecting the supporting members to an electronic circuit; 4) arranging the supporting member with the electronic circuit inside the ear plug housing; 5) connecting the skin contact parts from the outside of the ear plug housing to the supporting member through pre-arranged holes (e.g. pre-stamped holes) in the outer wall, such that the skin contact part and the supporting member are arranged for clamping the outer wall. This manufacturing method has found to be reliable and fast, especially in respect of providing ear plugs with individually positioned electrodes.

BRIEF DESCRIPTION OF THE DRAWINGS

Embodiments of the invention will now be explained in further detail with reference to the figures.

DETAILED DESCRIPTION OF THE INVENTION

Figure 1:
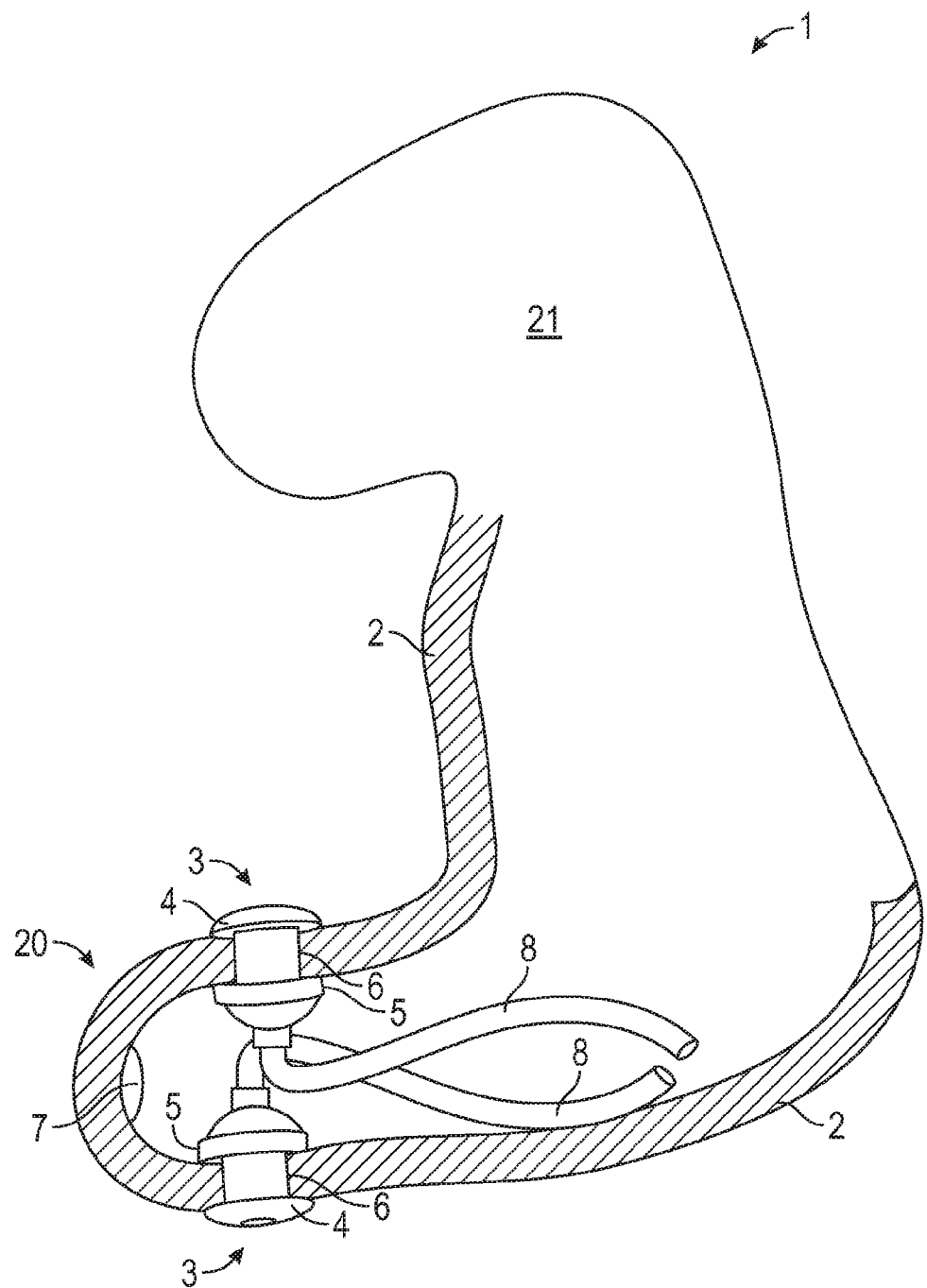
FIG. 1 illustrates an ear plug having EEG electrodes arranged in a housing made from a resilient material.

FIG. 1 shows an ear plug 1 which is supposed to be individually fitted to an ear canal of a person. A first part 20 of the ear plug 1 will be arranged in the ear canal and a second part 21 of the ear plug shown in FIG. 1 will be arranged in the concha region or outside the ear canal. In other embodiments the whole ear plug may be fitted into the ear canal. The ear plug 1 is shaped by a wall 2 made of a resilient material, e.g. silicone. Two EEG electrodes 3 are shown in the ear plug, but there could be three or four. Each EEG electrode comprises a skin contact part 4, which should obtain a good electrical contact with the skin of the person when the ear plug 1 is in use. The skin contact part 4 is arranged on the external side of the housing wall 2. The skin contact part 4 is connected by a connector 6, e.g. a metal pin, through the wall 2 to a supporting member 5 arranged on the inner side of the wall 2. The supporting member 5 may be in the form of a washer. The two electrodes shown are each connected with a wire 8 for transferring the detected EEG signal, or an amplified EEG signal, to an electronic module (not shown) for signal processing. This could be in a signal acquisition circuit, which typically holds an amplifier.

The ear plug shown in FIG. 1 could comprise more than the two EEG electrodes shown. There could be e.g. a total of at least three or at least four electrodes in the first part 20 of the ear plug placed in the ear canal. Also, or alternatively, there could be an electrode in the second part 21 of the ear plug arranged e.g. in the concha. This concha electrode could function as a reference electrode. The ear plug in FIG. 1 is further provided with an opening 7 for an acoustic sound passage, in order to allow for normal hearing for the person wearing the ear plug.

The housing wall 2, made from a resilient and soft material, may be the structure providing the ear plug with its overall shape. The wall 2 should be designed such that it will press the skin contact part 4 of the electrodes against the skin in the ear canal. This pressure should be high enough to provide a stable electrical contact in order to detect an EEG signal. However, the pressure should not be such that the person carrying the ear plug becomes annoyed over long term use of the ear plug.

The thickness of the wall 2 could be constant for the entire ear plug. The thickness of the wall 2 may, however, also be varied in order to provide for a pressure being exerted by the EEG electrodes 3 against the skin, but no pressure being exerted by any other part of the ear plug. The wall should be thick enough to ensure that it stays in the correct shape without any risk of collapsing. Often the thickness will be in the range 0.5-3.0 mm.

The resilient material for the wall 2 may be an elastic material or a viscoelastic material. A possible material for the wall 2 is silicone, e.g. with a Shore hardness in the range 20-60, but other materials could also be applied.

It is also possible that the inside space of the ear plug could be filled with the resilient wall material, e.g. silicone, except for space for electronics, connecting wires or flex print and for an acoustic sound passage.

Figure 2:
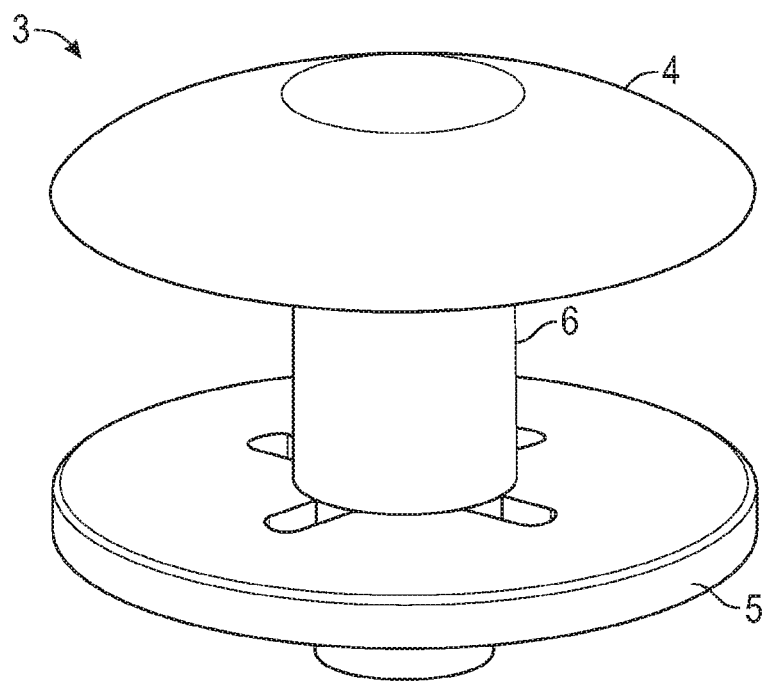
FIG. 2 illustrates an EEG electrode with a washer for holding the electrode.

FIG. 2 shows an example of an EEG electrode 3 comprising a skin contact part 4, a pin connecting part 6 and a supporting member 5. As also indicated in FIG. 1, the skin contact part and the supporting member 5 will be arranged for clamping the wall material of the ear plug housing, when assembled to the ear plug.

In the embodiment of an EEG electrode shown in FIG. 2 the skin contact part 4 are typically integrated with the connecting part 6, e.g. manufactured from the same piece of metal. The supporting member 5, e.g. a washer, is detachably connected to the connecting part 6. This construction of the EEG electrode facilitates an assembling method of the ear plug where the supporting members to all electrodes to be arranged in the ear plug are each first attached to a signal wire 8 which is connected to an electronic circuit, or, the supporting members are each directly connected to an electronic or a signal acquisition circuit, e.g. including a pre-amplifier, from which there is a connection to one electronic circuit. Then these supporting members 5, now connected through wires, are arranged inside an ear plug housing. Each supporting member is arranged on the inside of the ear plug housing wall at a location where the intention is to place an EEG electrode. A hole is made, e.g. stamped, in the wall, and the connecting part 6 is pressed through and engages, e.g. by a snap connection, with the supporting member 5.

In practice the wiring between the supporting members 5 and the electronic may be made by flexible printed circuit boards, in the following called flex print (see FIG. 8 and below). The supporting member 5, e.g. a washer, is then soldered to the flex print.

If the connecting part 6 has a cylindrical shape, as indicated in FIG. 2, a circumferential groove could be provided in order for the supporting member to click in correct position in this groove.

The embodiment in FIG. 2 is shown with the skin contact part 4 and the pin connecting part 6 centered on the same center axis. This is one possibility, but also different options are possible. E.g. the pin connecting part 6 could be arranged towards the outer circular edge of the skin contact part 4. Such a design will facilitate the manufacturing of a combined skin contact part 4 and pin connecting part 6 from one sheet material, where the combined skin contact part 4 and pin connecting part 6 are punched from the sheet material, after which the pin connecting part 6 is bent in an angle of 90 degrees or substantially 90 degrees in relation to the surface area of the skin contact part 4.

The skin contact part 4 is preferably made from a material giving a good electrical contact to the skin, being durable in the humid environment, and being nontoxic and not irritant to the skin. An example of a possible material could be titanium with a surface coating of iridium oxide. Further examples of materials are found in EP 1 237 621 B1, paragraph [0016]. Iridium oxide provides an electrode with relatively low skin contact impedance when used as dry electrode.

The pin connecting part 6 will often have a diameter of 1 mm if having a circular cross sectional shape. The diameter of the skin contact part can be in the range 3-4 mm, or in the range less than 3.5 mm. The thickness of the skin contact part will often be in the range of 0.25-0.5 mm.

Figure 3:
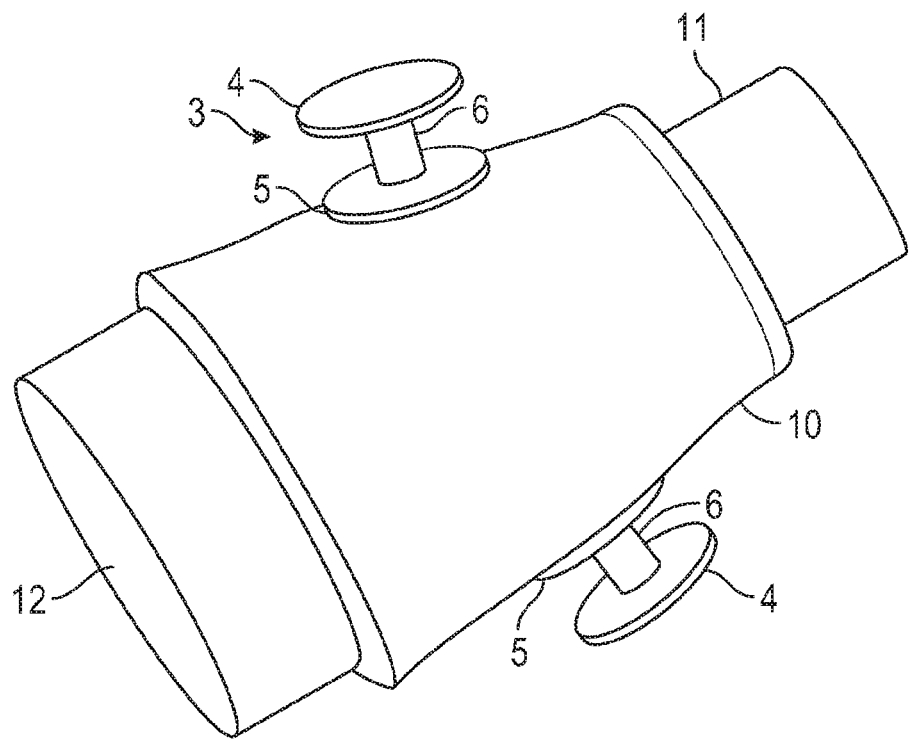
FIG. 3 illustrates an inner housing for an ear plug, where the inner housing has two extending EEG electrodes.

FIG. 3 shows an embodiment where an inner shell 10 is provided for the housing. The inner shell 10 is preferably made from a non resilient material, e.g. acrylic. The electrodes 3 can be arranged on this shell 10 with electrical connection to an electronic circuit, and with connection to wiring or a flex print arranged inside the shell 10.

After the inner shell 10 has been prepared with electrodes, electronic circuit and electrical connections in form of wires and/or flex print inside, the resilient outer wall 2 is arranged on the outside of the shell 10. The resilient outer wall 2 is pulled over the inner shell 10 with the electrodes 3, and subsequently the skin contact part 4 of the electrodes 3 are pressed through pre stamped holes in the resilient outer wall material. The outer wall material will need to be sufficiently elastic for this purpose. Alternatively, the resilient outer wall 2 may be casted directly on the inner shell.

Often the ear plug will be provided with a through going hole having a sufficient diameter not to obstruct the sound passage to the eardrum at a level where discernable occlusion of the sound is introduced. The position of this opening or hole is indicated by reference 12, and the opening continues through the extension 11 of the inner shell. The diameter of this opening or hole is at least 1.5 mm, preferably at least 2 mm, and more preferably at least 2.5 mm.

In general, all embodiments may be provided with a through going opening or hole in order not to obstruct the sound passage. The diameter may be as mentioned above, or, if the opening does not have a circular cross sectional shape, the cross sectional area may be at least 1.8 mm$^2$, preferably at least 3.2 mm$^2$, and more preferably at least 5.0 mm$^2$.

Figure 4:
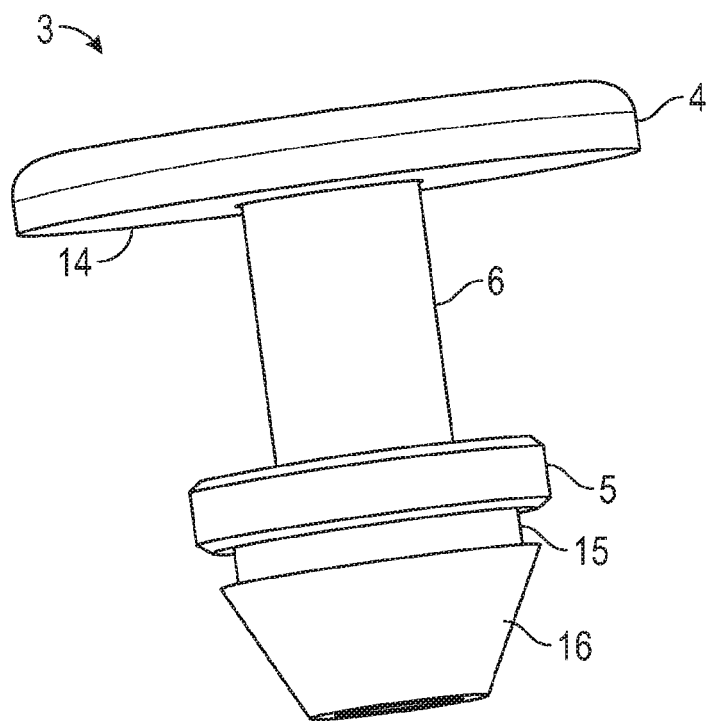
FIG. 4 illustrates an example of an EEG electrode without separate washer.

FIG. 4 shows an embodiment of the electrode 3 where the supporting member 5 is fixedly attached to the connector 6 and the supporting part is provided with a shape facilitating easily pressing the supporting member with the conical part 16 first through a stamped hole in the outer housing wall 2. The resilient housing wall 2 should be clamped between the supporting member 5 and the inner side 14 of the skin contact part 4 when positioned correctly. The material forming the hole in the resilient housing wall 2 should preferably also abut against the connector part 6 in order to limit the transport of dirt and humidity through any leaks around the connector part 6.

When the conical part 16 and the supporting member 5 have been pressed through the resilient housing wall it should be connected to the circuit inside the housing. A circumferential groove 15 may be applied for this connection.

Figure 5:
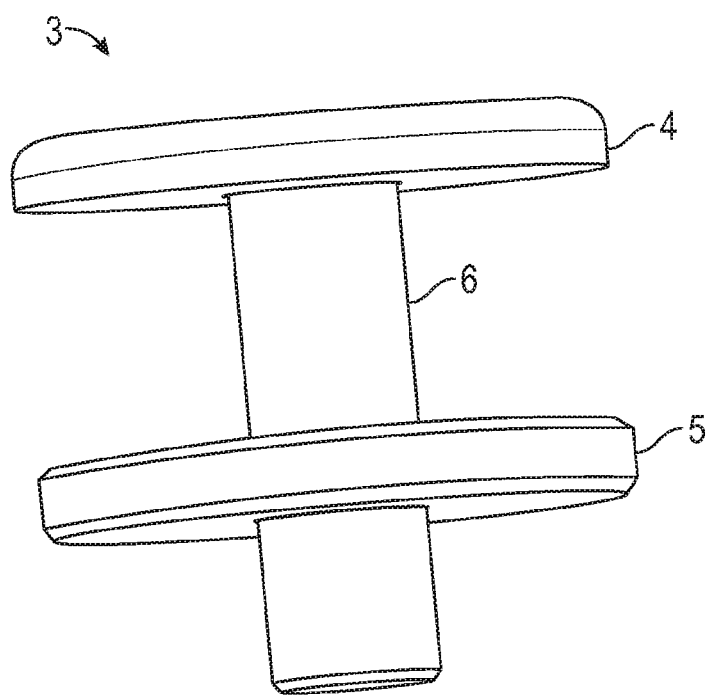
FIG. 5 illustrates a further example of an EEG electrode with a washer for holding the electrode.

FIG. 5 shows an electrode where the supporting member 5 is a washer for holding the electrode. As for the embodiment of FIG. 3 the washer 5 in FIG. 5 is first fixed to the electronics e.g. by a wire, or soldered directly to a flex print. Then the connector 6, which is attached to the skin contact part 4 is pushed through the resilient outer wall 2, e.g. through a pre stamped hole. The connector 6 and the washer 5 may be adapted for locking in a position where the washer 5 and the skin contact part 4 are clamping the resilient outer wall. The fixation of the connector 6 in the washer 5 may also be obtained by soldering or gluing. However, a good electrical contact between the two parts should be obtained.

Figure 6:
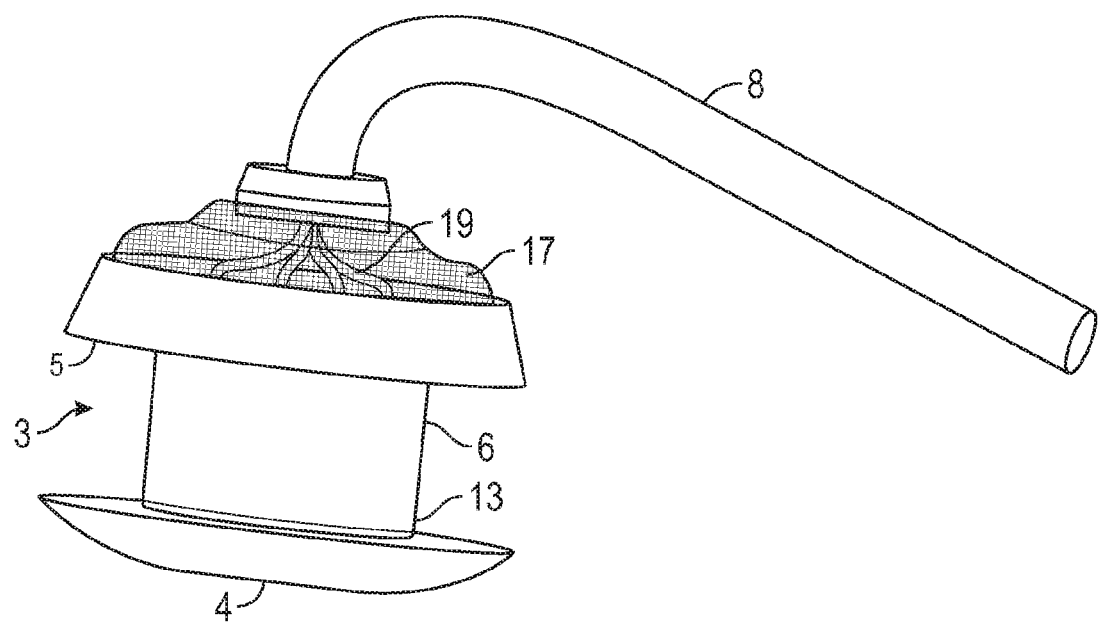
FIG. 6 illustrates an example of an EEG electrode comprising a module with an electronic circuit and connected with a signal cable.

FIG. 6 shows an embodiment of the electrode for the ear plug, where a signal acquisition circuit (not shown) comprising e.g. a pre-amplifier or an A/D converter is arranged in the supporting member 5 or in the connecting member 6. The connecting member 6 comprises an inner connecting part 61 (see FIG. 9) and an outer connecting part 62, where the inner connecting part 61 is integral with the skin contact part 4, e.g. shaped from the same piece of material. The outer connecting part 62 is integral with the supporting member 5, and forms an electronic housing 25 (see FIGS. 8 and 9) which is made from an electrically insulating material, e.g. a ceramic, a polymer or different types of plastic, coated on its outer surface with a conductive layer in order to obtain electromagnetic shielding of electronic circuit and any signal path. There is a band 13 around the outer connecting part 62, where there is no conductive layer, in order to insulate the electrode or the skin contact part 4 from the shielding, so that the EEG signal is not short circuited. In FIG. 6 wires 19 from the connecting cable 8 are seen. Also a sealant 17, e.g. glue, for protection of the wires, is shown. The shielding of the supporting member 5 will also provide some protection of the skin contact part 4 against electromagnetic noise. The shielding may be active or passive, where active shielding is that the shield is provided with the same potential as the signal wire and consequently there is no potential between the signal wire and the shield. WO 2013/026481 A1 describes this.

Figure 7:
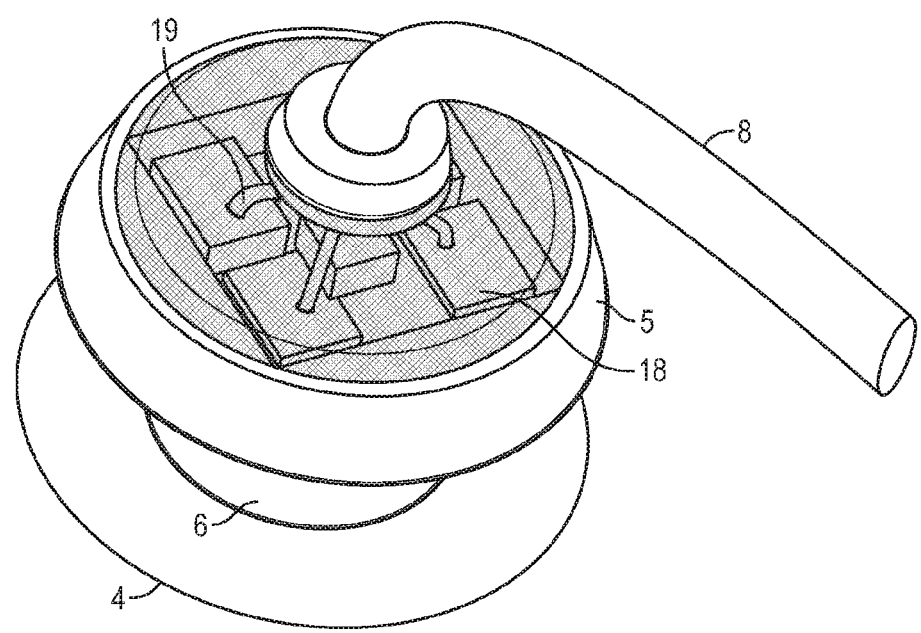
FIG. 7 illustrates the EEG electrode of FIG. 6 from a different viewing angle.

FIG. 7 shows the electrode of FIG. 6, but from a different angle, thereby illustrating the wires 19 connecting to pads 18 on a circuit board (e.g. a thick film circuit board). FIG. 8 illustrates three electrodes 3 for an ear plug connected by flex print connections 8. The electrodes are here illustrated (partly in exploded views) as active electrodes, meaning that a signal acquisition circuit, e.g. comprising an amplifier and/or an A/D converter, is arranged at, or behind, the skin contact part, which is also what FIGS. 6 and 7 show. The active electrodes need power supply lines as well as signal lines through the flex print connections 8. The flexibility of the flex print connections 8 means that the electrodes 3 can be placed individually in the ear plug 1. This can be an advantage in connection with customized ear plugs since different persons have different ear channels, and the optimal positions for best detecting an EEG signal in the ear canal may be different from person to person. Also, the difference in geometry of the ear channels of different persons may necessitate different positions of the electrodes.

Figure 8:
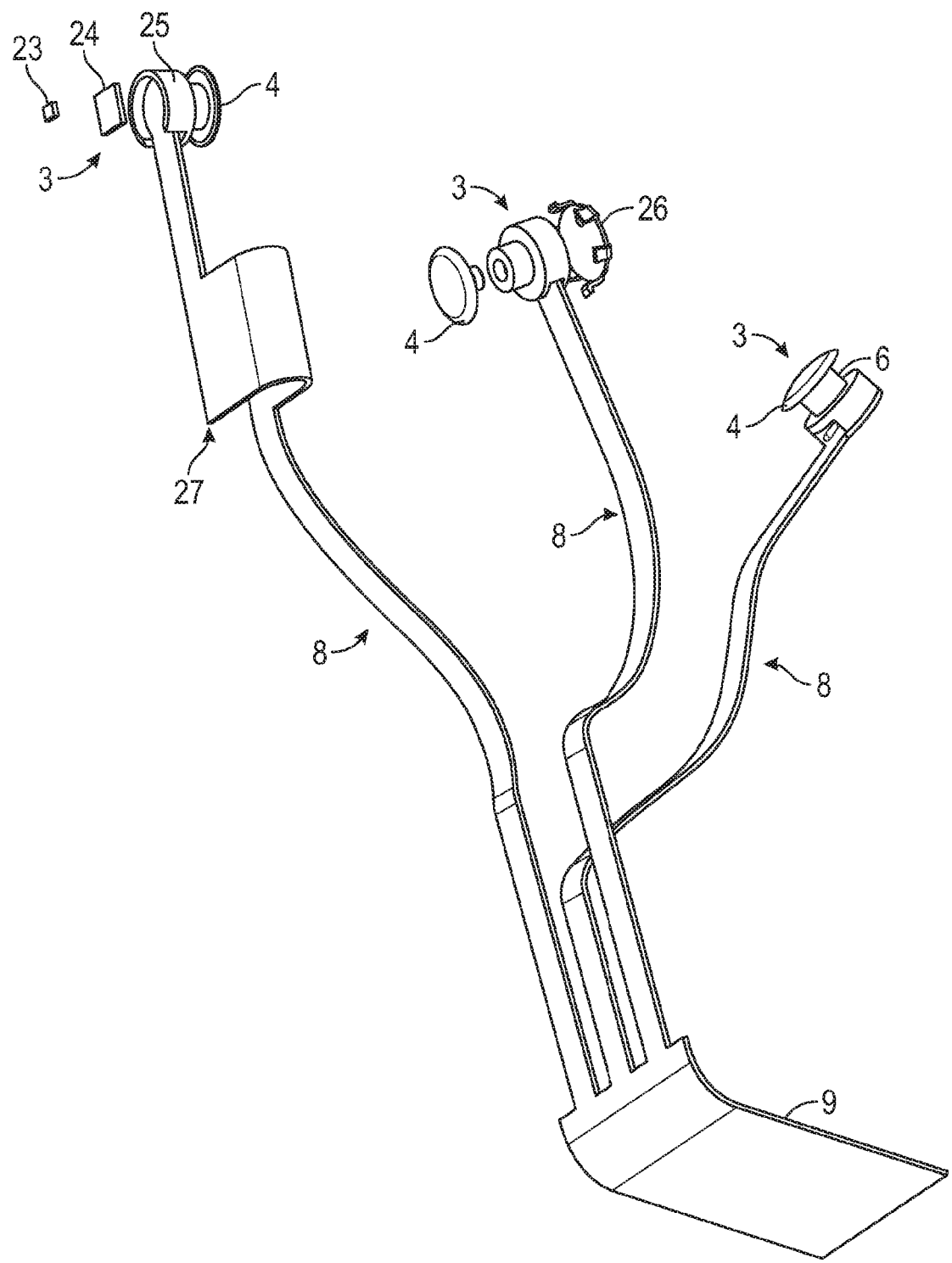
FIG. 8 illustrates a flex print connected to three different EEG electrodes.

The bending 27 in one of the three flex print connections in FIG. 8 makes it possible to mount all electrodes and supporting members on the same side of a flat flex print piece, and still let one of the electrodes face in the opposite direction when mounting the flex print in the ear plug.

The flex print connections of FIG. 8 may also be applied in connection with passive electrodes, where amplifiers, A/D converters etc. could be arranged at a central flex print part 9, to which the different flex print connections 8 are connected. In such an embodiment shielding of the signal wires on the flex print connections 8 may be preferred.

The ear plug in the different embodiments described may be made as a customized ear plug by fitting the size and shape exactly to the size and shape of the ear canal of the person to use the ear plug. The ear plug can also be made as a standard ear plug in different preselected sizes, where each person will have to select the size fitting best. The resiliency of the outer wall of the ear plug will facilitate the use of standard sizes, since each standard size ear plug can be slightly compressed and will therefor fit a smaller range of ear canal sizes.

Figure 9:
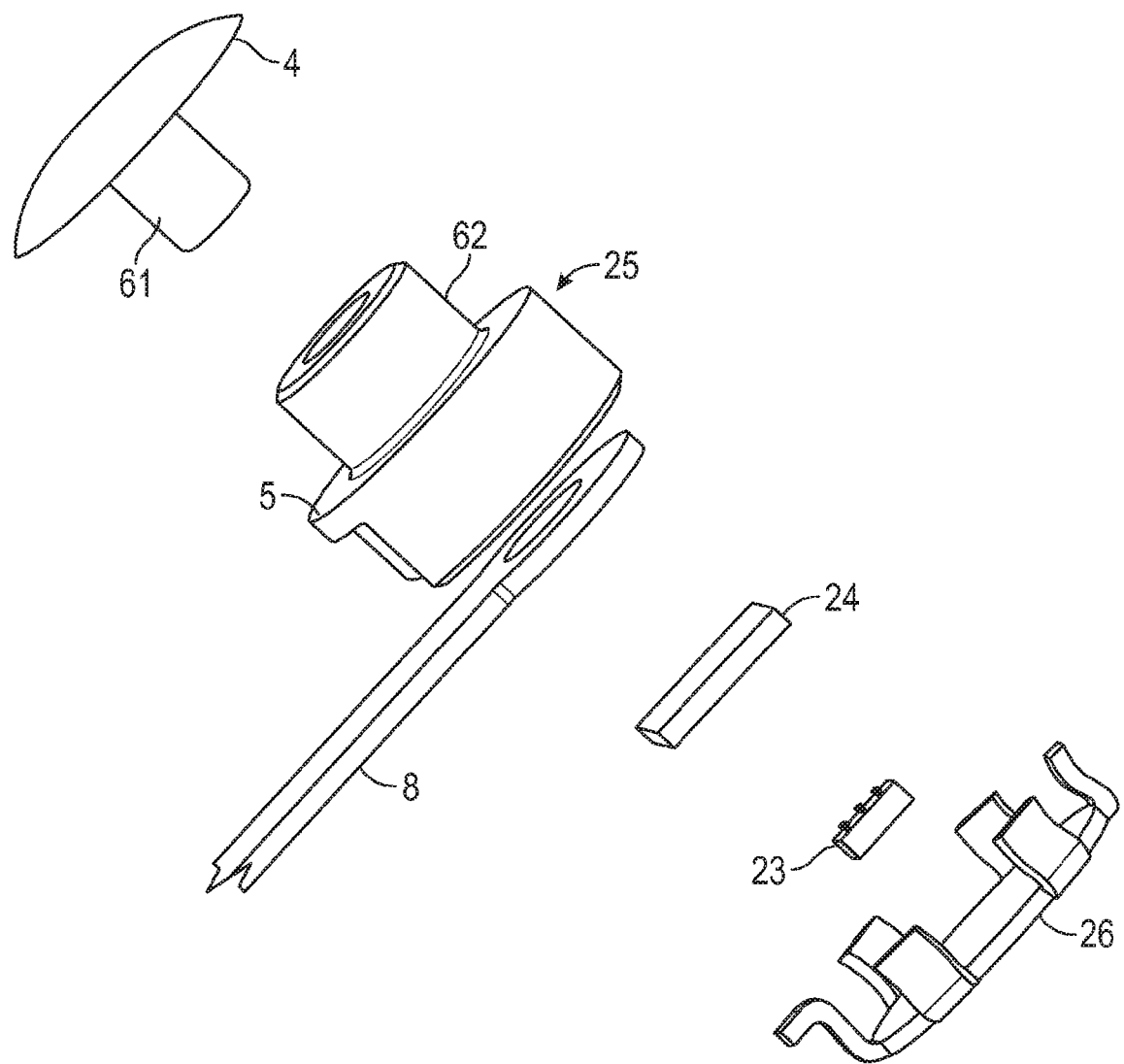
FIG. 9 illustrates an exploded view of an EEG electrode.
Figure 10:
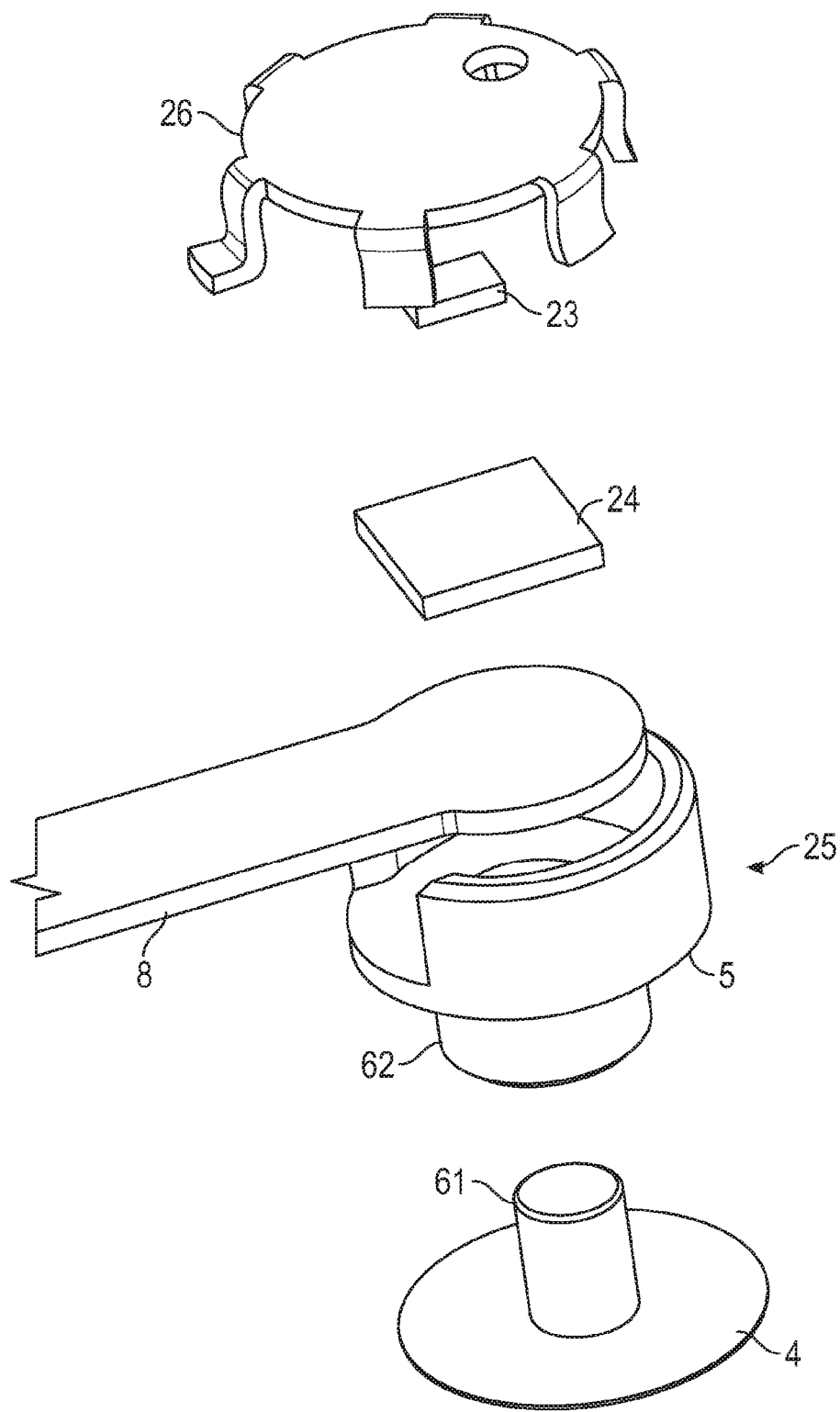
FIG. 10 illustrates the exploded view of an electrode from FIG. 9 but seen from a different angle.

FIGS. 9 and 10 shows enlarged exploded views of the electrodes from FIG. 8. The electrode comprises the skin contact part 4 integrated with the inner connecting part 61. This may be made from titanium with a surface coating of iridium oxide, e.g. only on or primarily on the surface intended to be in contact with the skin. The amplifying circuit is arranged on a chip 23. This chip may also comprise and A/D converter. The chip is placed on a circuit board 24 which is arranged in the electronic housing 25. The electronic housing 25 is provided with a shielding layer made from an electrically conductive material as mentioned above. The electronic housing 25 comprises the outer connecting part 62 as well as the supporting member 5, which two parts are integrally connected, e.g. made from the same piece of material.

A flex print connecting part 8 may also be connected to the electronic housing 25 and to the circuit board 24 (which could be a thick film module) comprising a chip 23 and possibly also other components. A cover 26 is arranged for covering the circuit board 24 and chip 23, and is made from, or coated with a conductive material in order to ensure a complete shielding of the electronic. The cover 26 is preferably also connected to neutral or ground on the flex print connector 8.

In the manufacturing of an ear plug comprising electrodes according to embodiments of FIGS. 6-10 there are at least two possibilities. The first is that the skin contact part 4 of the fully assembled electrode 3 is pushed through holes in the resilient, and elastic, outer wall material. The second is that the electrode before assembly is in two parts, one with the electronic housing 25 with amplifying circuit chip 23 electronic circuit board 24, and connections 8, and the other part being the skin contact part 4 with the inner connecting part 61. The ear plug is then assembled by pushing the outer connecting part 62 into holes in the resilient outer wall from the inside of the ear plug, and then pushing the skin contact part 4 with the inner connecting part 61 into the outer connecting part 62 from the outside of the ear plug.

One advantage of providing the ear plug of FIG. 1 with an electrode according to FIG. 2, FIG. 4-7 or FIG. 9-10, is that when these electrodes are only connected by a thin or flexible wire or flex print, they will not affect the flexibility and compressibility of the ear plug housing or the outer wall 2 of this housing. I.e. the overall flexibility or resiliency which the resilient wall 2 can provide to the ear plug, can be maintained when supplying the ear plug with electrodes according to these figures or similar types, and where these electrodes are connected to electronic circuits by flexible wires or flex print. In this way the electrodes will follow movements of the outer wall, both when the ear plug is compressed and when the ear plug exerts a pressure on the skin in the ear canal.

As mentioned a preferred thickness of the wall 2 is 0.5-3 mm. But the inner part of the ear plug can also be filled with the same resilient material as the material used for the wall 2. This filling may leave space for a ventilation and sound passage channel. The ear plug with all resilient material may be casted in one process around the electrodes, supporting members, electronic circuit and connections.

Figure 11:
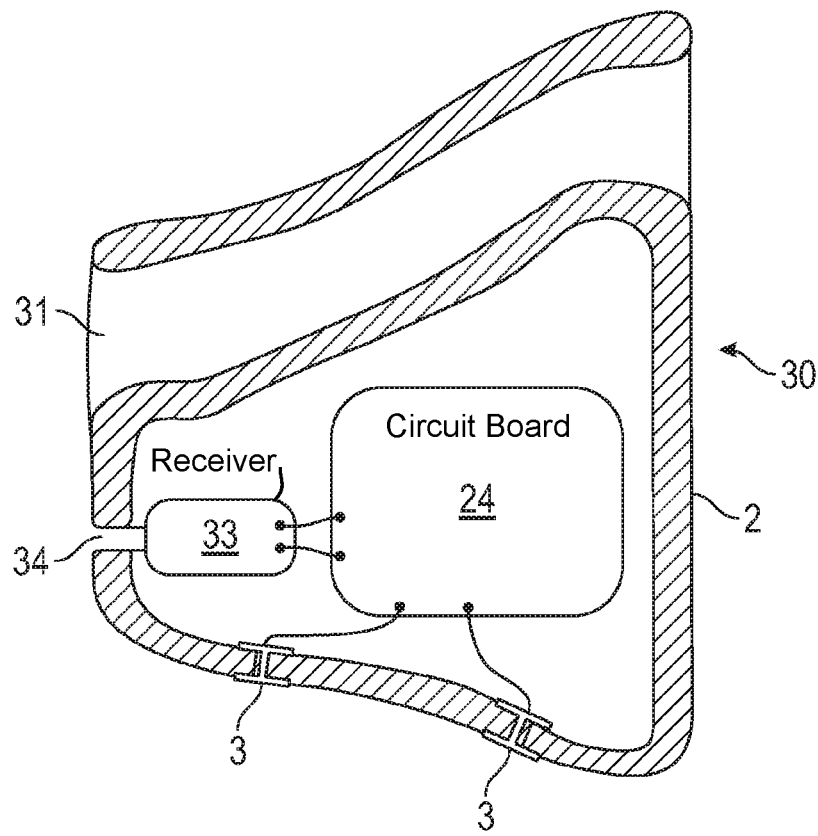
FIG. 11 illustrates an EEG monitor based on an ear plug with EEG electrodes arranged in a resilient wall.

FIG. 11 shows an example of an EEG monitor 30 built into an ear plug 1 with a resilient outer wall 2, an electronic circuit 24 connected with two EEG electrodes 3 and an acoustic sound passage 31. The EEG monitor is adapted for placement in the ear canal, and it is provided with a speaker (receiver) 33 at a sound opening 34. The speaker can be applied for providing alarms or notifications to the person wearing the EEG monitor 30. The end of the EEG monitor provided with the sound opening 34 is intended to face the inner part of the ear canal, i.e. the eardrum, when in use.

Figure 12:
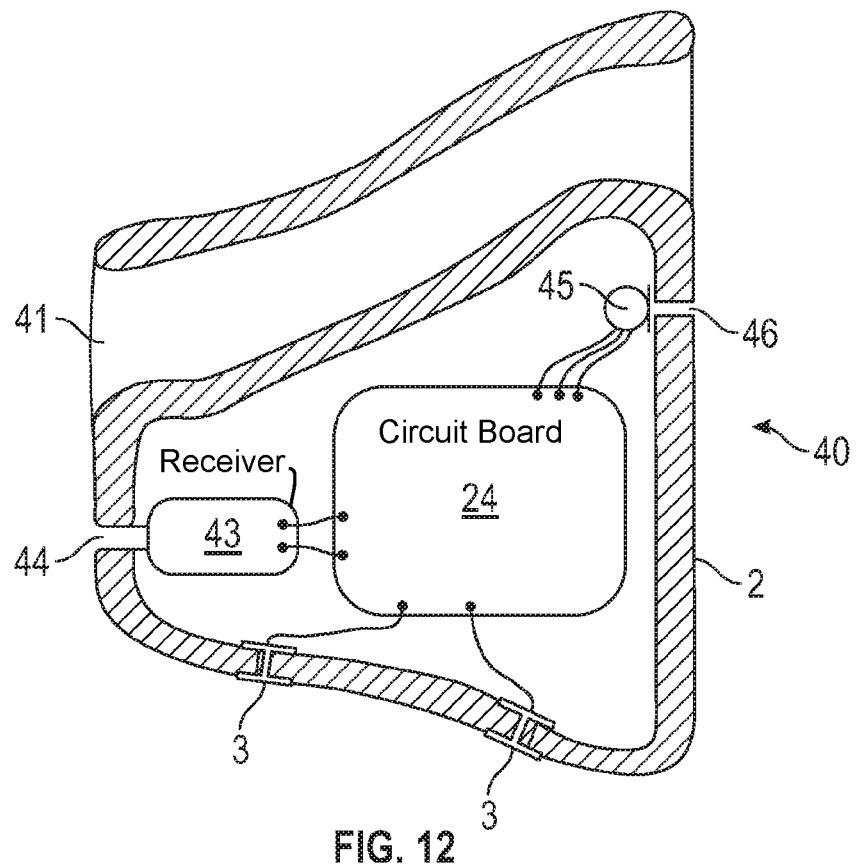
FIG. 12 illustrates a hearing aid comprising an ear plug with EEG electrodes.

FIG. 12 shows an example of a hearing aid 40 built into an ear plug 1 with a resilient outer wall 2 and provided with EEG electrodes 3. The hearing aid 40 is provided with a microphone 45 arranged at a microphone inlet 46. The microphone is connected to an electronic circuit 24 provided with means for sound amplification and processing (not shown). The circuit 24 delivers a processed signal to a receiver 43 generating an acoustic sound through the sound opening 44, which is facing the eardrum when the hearing aid 40 is arranged in the ear canal. The hearing aid further comprises a vent 41 for reducing the occlusion effect of the hearing aid.

In a hearing aid, detection and analysis of the hearing aid user's EEG signal may be applied for adjustment of the hearing aid. This could be as described in WO 2011/006681 A1.

The invention claimed is:

1. An ear plug for arrangement in an ear canal, the ear plug comprising
   at least two electrodes prepared for detecting an EEG signal from a skin surface when the ear plug is arranged in the ear canal,
   a flexible connection element combining the signals from the at least two electrodes,
   a housing having an outer wall made from a resilient material, and
   at least one amplifying circuit in said housing and connected to said flexible connection element for processing said EEG signal detected by said electrodes,
   the electrodes being provided with a skin contact part arranged on an outside surface of the housing and connected through the outer wall of the housing to a supporting member on an inner part of the housing, the skin contact part and the supporting member being arranged for clamping the outer wall.

2. The ear plug according to claim 1, wherein the housing is compressible and the electrodes are arranged to follow a movement caused by a compression of the outer wall.

3. The ear plug according to claim 1, wherein the outer wall is provided with a shape customized to the ear canal of an intended user.

4. The ear plug according to claim 1, wherein the skin contact part of the electrodes is provided with a layer of iridium oxide on at least the surface intended to touch the skin surface.

5. The ear plug according to claim 4, wherein the layer of iridium oxide also comprises tantalum.

6. The ear plug according to claim 4, wherein the layer of iridium oxide is porous.

7. The ear plug according to claim 1, wherein said at least one amplifying circuit comprises a separate amplifying circuit for each one of the at least two electrodes, the amplifying circuits being shielded against electromagnetic interference.

8. The ear plug according to claim 1, wherein the flexible connection element comprises a flex print circuit.

9. The ear plug according to claim 1, wherein the skin contact part is detachably connected to the supporting member by a connecting part.

10. The ear plug according to claim 1, wherein the amplifying circuit is a signal acquisition circuit that comprises an A/D converter.

11. The ear plug according to claim 1, wherein the outer wall is adapted to exert a pressure against the ear canal wall when inserted, in order to enhance electrical contact between the skin contact parts of the at least two electrodes and the ear canal wall.

12. An EEG monitor comprising an ear plug according to claim 1, and a signal processor for processing signals obtained from said at least one amplifying circuit.

13. The ear plug according to claim 1, wherein said flexible connection element comprises flexible wires.

14. The ear plug according to claim 1, wherein said skin contact part and supporting member clamp said outer wall with said skin contact part in contact with an outer surface of said outer wall and said supporting member in contact with an inner surface of said outer wall, and wherein for at least one of said electrodes, a surface of the supporting member in contact with said inner surface of said outer wall is of smaller surface area than a surface area of said skin contact part in contact with said outer surface of said outer wall.

15. The ear plug according to claim 1, wherein said skin contact part and supporting member clamp said outer wall with said skin contact part in contact with an outer surface of said outer wall and said supporting member in contact with an inner surface of said outer wall, and said ear plug further including circuit elements mounted to a back side of the supporting member opposite a side of said supporting member contacting said inner surface of said outer wall.

16. The ear plug according to claim 1, wherein said skin contact part includes a tapered portion configured to be pressed through a pre-arranged hole in said outer wall to engage said supporting member to provide said clamping.

17. A hearing aid comprising a microphone for converting sound to electrical signals, processing circuitry for processing said electrical signals to compensate for a hearing impairment, and an output transducer for producing sound based on the processed electrical signals, said hearing aid further comprising an ear plug according to claim 1.

18. A method for manufacturing an EEG monitor comprising the steps of:
providing an ear plug housing having a resilient outer wall,
providing at least one EEG electrode, separated into a skin contact part and a supporting member,
connecting the supporting member to an electronic circuit via a flexible connection element, arranging the supporting member with the electronic circuit inside the ear plug housing,
connecting the skin contact part from the outside of the ear plug housing to the supporting member through a pre-arranged hole in the outer wall, such that the skin contact part and the supporting member are arranged for clamping the outer wall.

19. The method according to claim 18, wherein said step of connecting the skin contact part to the supporting member comprises supporting one of said skin contact part and supporting member while pressing the other of said skin contact and supporting member through said pre-arranged hole to engage said skin contact part and supporting member.

* * * * *